United States Patent
Abrunhosa et al.

(10) Patent No.: US 10,600,528 B2
(45) Date of Patent: Mar. 24, 2020

(54) PROCESS FOR PRODUCING GALLIUM-68 THROUGH THE IRRADIATION OF A SOLUTION TARGET

(71) Applicant: Ion Beam Applications S.A., Louvain-la-Neuve (BE)

(72) Inventors: Antero Abrunhosa, Coimbra (PT); Vitor Alves, Coimbra (PT); Francisco Alves, Coimbra (PT)

(73) Assignee: Ion Beam Applications S.A., Louvain-la-Neuve (BE)

( * ) Notice: Subject to any disclaimer, the term of this patent is extended or adjusted under 35 U.S.C. 154(b) by 67 days.

(21) Appl. No.: 15/998,846

(22) Filed: Aug. 17, 2018

(65) Prior Publication Data

US 2019/0013108 A1   Jan. 10, 2019

Related U.S. Application Data

(62) Division of application No. 15/172,905, filed on Jun. 3, 2016.

(30) Foreign Application Priority Data

Jun. 5, 2015   (EP) ..................................... 15170854

(51) Int. Cl.
   *G21G 1/00*   (2006.01)
   *B01J 47/00*   (2017.01)
   (Continued)

(52) U.S. Cl.
   CPC ........... *G21G 1/001* (2013.01); *A61K 51/088* (2013.01); *B01J 39/05* (2017.01); *B01J 39/18* (2013.01);
   (Continued)

(58) Field of Classification Search
   CPC combination set(s) only.
   See application file for complete search history.

(56) References Cited

U.S. PATENT DOCUMENTS

| | | | | |
|---|---|---|---|---|
| 7,728,310 B2* | 6/2010 | Fitzsimmons | ......... | G21G 1/001 250/432 PD |
| 8,894,860 B2* | 11/2014 | Li | ........................ | B01D 15/361 210/661 |
| 2008/0035542 A1* | 2/2008 | Mourtada | ............ | G21G 1/0005 210/143 |

FOREIGN PATENT DOCUMENTS

| EP | 1 343 533 A1 | 9/2003 |
|---|---|---|
| WO | WO 02/051447 A1 | 7/2002 |
| WO | WO 2012/055970 A1 | 5/2012 |

OTHER PUBLICATIONS

Pandey et al. ("Cyclotron production of 68Ga via the 68Zn(p,n)68Ga reaction in aqueous solution"; Am J Nucl Med Mol Imaging; 2014; 4(4); pp. 303-310). (Year: 2014).*

(Continued)

*Primary Examiner* — Ryan B Huang
(74) *Attorney, Agent, or Firm* — Finnegan, Henderson, Farabow, Garrett & Dunner LLP (57) ABSTRACT

The present disclosure relates to a process for purifying and concentrating $^{68}$Ga isotope produced by irradiation with an accelerated particle beam of a $^{68}$Zn target in solution. The process according to the present disclosure allows for the production of pure and concentrated $^{68}$Ga isotope in hydrochloric acid solution. The present disclosure also relates to a disposable cassette for performing the steps of purification and concentration of the process.

20 Claims, 3 Drawing Sheets

(51) Int. Cl.
    *B01J 41/05*         (2017.01)
    *G21G 1/10*         (2006.01)
    *C22B 58/00*        (2006.01)
    *C07B 59/00*        (2006.01)
    *B01J 41/12*         (2017.01)
    *B01J 39/18*         (2017.01)
    *B01J 39/05*         (2017.01)
    *A61K 51/08*        (2006.01)

(52) U.S. Cl.
    CPC ............... *B01J 41/05* (2017.01); *B01J 41/12* (2013.01); *B01J 47/00* (2013.01); *C07B 59/008* (2013.01); *C22B 58/00* (2013.01); *G21G 1/10* (2013.01); *C07B 2200/05* (2013.01); *G21G 2001/0021* (2013.01)

(56) References Cited

OTHER PUBLICATIONS

Meyer et al. ("68Ga-labelled DOTA-derivatised peptide ligands"; Eur J Nuc Med Mol Imag; 2004; 31(8); pp. 1097-1104). (Year: 2004).*
Rosch ("Past, present and future of 68Ge/68Ga generators"; Applied Radiation and Isotopes; 2013; 76; p. 24-30). (Year: 2013).*
Velikyan ("Prospective of 68Ga-Radiopharmaceutical Development"; Thernaostics 2014; 4(1); p. 47-80). (Year: 2014).*
International Search Report for EP Application No. 15170854.2, filed Jun. 5, 2015.
Mukesh, Pandey et al., "Cyclotron production of (68) Ga via the (68)Zn(p,n)(68)Ga reaction in aqueous solution," Am. J. Nucl. Med. Mol. Imaging 2014, vol. 4, No. 4, Jun. 15, 2014.

* cited by examiner

PROCESS FOR PRODUCING GALLIUM-68 THROUGH THE IRRADIATION OF A SOLUTION TARGET

CROSS REFERENCE TO RELATED APPLICATIONS

This application is a divisional application of and claims the benefit of priority from U.S. application Ser. No. 15/172,905, filed Jun. 3, 2016, which is based upon and claims the benefit of prior European Patent Application No. 15170854.2, filed on Jun. 5, 2015. The above referenced applications are hereby incorporated by reference in their entireties.

TECHNICAL FIELD

The present invention relates generally to the field of radiopharmaceutical production. More particularly, the present invention relates to a process for the production of $^{68}$Gallium radioisotope from a suitable solution target irradiated by an accelerated particle beam.

The invention also relates to a disposable cartridge for purifying and concentrating the Gallium-68 produced by the irradiation of a isotopically enriched Zinc solution target by an accelerated particle beam.

DESCRIPTION OF RELATED ART

Gallium-68 ($^{68}$Ga) is of special interest for the production of Ga-radiolabelled compounds used as tracer molecules in positron emission tomography (PET) imaging technique. $^{68}$Ga forms stable complexes with chelating agents, like DOTA (1,4,7,10-tetraazacyclododecane-1,4,7,10-tetraacetic acid), NOTA (1,4,7-triazacyclononane-1,4,7-triacetic acid) and HBED-CC (N,N'-bis-[2-hydroxy-5-(carboxyethyl)benzyl]ethylenediamine-N,N'-diaceticacid) for example. $^{68}$Gallium tracers may be used for brain, heart, bone, lung or tumor imaging.

To obtain $^{68}$Ga, the most common technique is the use of a $^{68}$Ge/$^{68}$Ga generator. Unfortunately, $^{68}$Ge/$^{68}$Ga generators can only produce small quantities of $^{68}$Ga per elution, suffer from limited lifetime and present the risk of contaminating the final preparation with the long-lived parent nuclide $^{68}$Ge.

Traditionally, $^{68}$Ga is also produced in a cyclotron via the $^{68}$Zn(pp,n)$^{68}$Ga reaction in a metal (solid) target. In short, the parent compound $^{68}$Zn is deposited as solid phase on a metallic substrate that is irradiated with a proton beam. After irradiation, the target is dissolved in a strong acid solution to obtain a solution that is then purified to obtain $^{68}$Ga. The process involves many time consuming steps, requires expensive hardware including solid targets and special systems to transport the irradiated target from cyclotron to the processing area and poses radioprotection issues of handling the materials after irradiation as well as liquid waste handling. This process is prone to contamination by metallic ions that can compromise the purification of the $^{68}$Ga and subsequent labeling reaction.

Alternative methods have been proposed to simplify and improve the process of $^{68}$Ga production by a cyclotron. For example, Pandey et al., (Am J Nucl Med Mol Imaging 2014;4(4):303-310) discloses the cyclotron production of $^{68}$Ga via a $^{68}$Zn(p,n)$^{68}$Ga reaction in aqueous solution. After irradiation of the $^{68}$Zn(NO$_3$)$_2$ target in solution, $^{68}$Ga is purified by passing the irradiated solution through a cation-exchange column, wherein $^{68}$Zn and $^{68}$Ga radioisotopes are trapped. The cation-exchange column is afterwards washed, and a step of elution of $^{68}$Zn is performed in order to recover the $^{68}$Zn that can be purified afterwards and used in a next irradiation. A final elution of $^{68}$Ga is thereafter performed with 3N HCl to a product vial.

Although the process presents some advantages over the traditional irradiation of solid targets, there is a need for an improved process, especially regarding the quantity of $^{68}$Ga produced, the overall time needed to perform the process and the purity of the final gallium in order to provide an economically viable alternative to $^{68}$Ge/$^{68}$Ga generators. For suitable chelating of the $^{68}$Ga it is especially important to avoid any metal ions in the final solution.

SUMMARY OF THE INVENTION

The invention is defined by the independent claims. The dependent claims define advantageous embodiments.

The present invention aims at providing a process that overcomes the above-discussed drawbacks of the prior art.

In particular, it is an object of the present invention to provide an efficient and reliable process for producing and purifying $^{68}$Ga isotope from a solution comprising zinc irradiated by an accelerated particle beam, like a proton beam. It is a further objet of the invention to achieve a high yield in the production of $^{68}$Gallium. It is a further object of the invention to provide a process with low contaminants concentration, especially metal ions.

To this end, the process according to the invention comprises the following steps:
  a) irradiating a target containing a target solution comprising Zinc using an accelerated particle beam,
  b) feeding the irradiated target solution into a strong cation exchanger,
  c) washing the strong cation exchanger,
  d) eluting Zinc isotopes from the strong cation exchanger with a Zinc elution solution comprising acetone,
  e) washing the strong cation exchanger,
  f) eluting $^{68}$Gallium isotope from the strong cation exchanger with hydrochloric acid solution to obtain an eluted solution,
  g) feeding said eluted solution into a strong anion exchanger
  h) washing the strong anion exchanger,
  i) eluting $^{68}$Gallium isotope from the strong anion exchanger with hydrochloric acid solution to obtain a final solution.

The process is characterized in that a step of diluting the irradiated target solution comprising zinc with water is performed after irradiation of the target solution comprising zinc and before feeding the irradiated target solution into the strong cation exchanger, the irradiated target solution being diluted at least 5 times its volume with water.

Indeed, the authors have surprisingly found that the overall quantity of $^{68}$Ga radionucleide recovered after separation and purification is greatly enhanced when the irradiated target solution is diluted at least 5 times its volume with water. The inventors have surprisingly found that, when the irradiated target is diluted 5 volume times, the retention of $^{68}$Gallium on the strong cation exchanger is greatly improved and the majority of $^{68}$Gallium is adsorbed on the exchanger, while the Zinc tends towards being eluted more easily. Accordingly, the overall yield of the process is greatly improved. The overall quantity of $^{68}$Ga purified and recovered by the method according to the invention allows an economically viable process to produce $^{68}$Ga for the facilities that have a particle accelerator like a cyclotron on-site.

In a preferred embodiment, the eluted solution comprising $^{68}$Ga is complemented with hydrochloric acid solution to obtain a complemented solution, this complementation being performed before feeding said eluted solution into the strong anion exchanger.

The authors have also found that the overall quantity of $^{68}$Ga isotope present in the final solution is more important when the eluted solution is, after elution from the strong cation exchanger, complemented with hydrochloric acid solution. This step allows adjusting the pH of the eluted solution, leading to a more efficient process.

It is also an object of the present invention to provide a disposable cassette for performing the steps of purification and concentration of $^{68}$Ga isotope after the irradiation of the solution target by an accelerated particle beam. There is a need for a disposable cassette that enables correct implementation of the method for purifying and concentrating Gallium-68. The disposable cassette should be used easily, and should be easy to maintain and service. The disposable cassette according to the invention may be used in connection with a device for synthesis of radiopharmaceuticals products.

To this end, a disposable cassette according to the invention comprises:
- a first conduit of which a first end is connected to an inlet of a strong cationic exchanger, said first conduit furthermore comprising one or more first 3-way valve,
- at least three first bottles containing chemical reagents being connected to the one or more first 3-way valve,
- an outlet of the strong cationic exchanger being connected by a second conduit to an elution vial, said second conduit comprising a second 3-way valve that is connected to a first waste vial,
- the elution vial being connected by a third conduit to an inlet of a strong anionic exchanger,
- the third conduit comprising a third 3-way valve that is connected to at least two second bottles containing chemical reagents,
- n outlet of the strong anionic exchanger being connected by a fourth conduit to a final solution vial, said fourth conduit comprising a fourth 3-way valve that is connected to a second waste vial.

The cassette furthermore comprises a dilution vial connected by a fifth conduit to a bottle containing water. The disposable cassette is furthermore characterized in that the dilution vial is connected by a sixth conduit to the outlet of a target containing a target solution comprising zinc. The disposable cassette is furthermore characterized in that the first conduit comprises a second end connected to the dilution vial.

Such disposable cassette is particularly suitable for performing the purification and concentration steps of a method according to the invention.

BRIEF DESCRIPTION OF THE DRAWINGS

These and further aspects of the invention will be explained in greater detail by way of examples and with reference to the accompanying drawings in which.

The drawings of the figures are neither drawn to scale nor proportioned. Generally, similar or identical components are denoted by the same reference numerals in the figures.

DETAILED DESCRIPTION OF EMBODIMENTS OF THE INVENTION

According to a first aspect of the invention, it is provided a process for producing and purifying $^{68}$Gallium from a target solution comprising zinc irradiated by an accelerated particle beam. Preferentially the target solution is a target solution comprising $^{68}$Zn, and more preferentially a target solution comprising isotopically enriched $^{68}$Z. Preferentially, the target solution is irradiated by a proton beam. The present invention is intended to be used preferably with a cyclotron apparatus, which delivers high energy proton beams.

Figure 1:
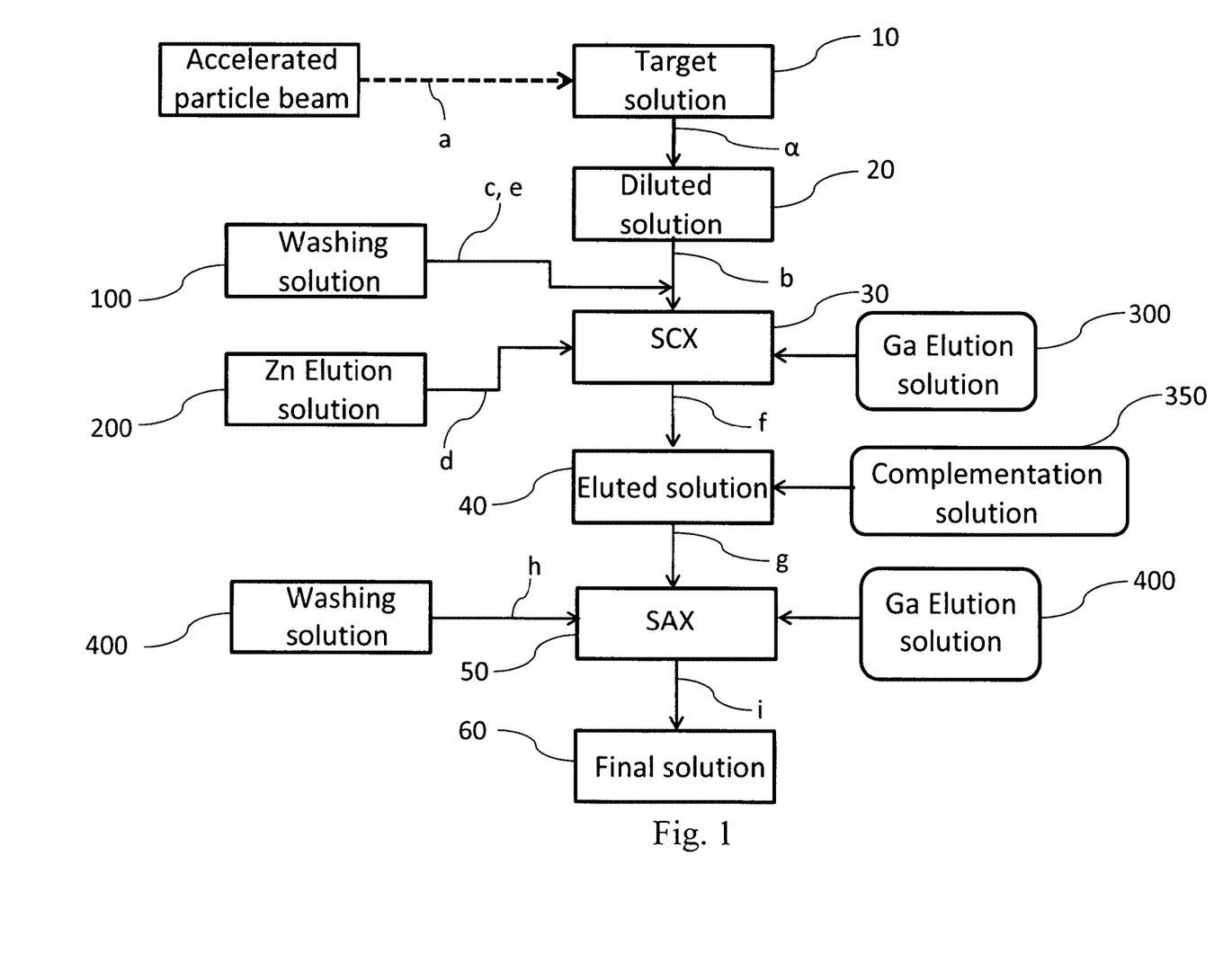
FIG. 1 shows a flow chart which represents a process according to the invention.

A flow chart of the process according to the invention is illustrated on FIG. 1. First, a target containing a target solution (10) comprising zinc, preferentially an isotopically enriched zinc-68 solution, is irradiated by an accelerated particle beam (step a). The target solution (10) may comprises a zinc salt selected among zinc nitrate, zinc chloride, zinc chlorate, zinc bromide, zinc iodide, zinc sulfate. The zinc salt may be diluted in nitric acid or hydrochloric acid. As an example, the target solution (10) is a Zinc-68 nitrate solution diluted in low concentrated nitric acid solution, for avoiding precipitation of zinc nitrate. For example, the target is an isotopically enriched 1.7 M solution of $^{68}$zinc nitrate in 0.2 N nitric acid in a closed target system. The target may for example be any Nirta® Conical target sold by Ion Beam Applications, Louvain-La-Neuve, Belgium. The target system may also be the target system as described in international patent publication WO 2012/055970. The target containing the target solution (20) is irradiated by an accelerated particle beam. Preferentially, the accelerated particle beam is a proton beam when the zinc target is isotopically enriched $^{68}$Zn. More preferentially, the proton beam is produced by a cyclotron, for example a low or mid energy cyclotron producing a proton beam in the range of 12 to 30 MeV. The irradiation step may last around 30 min at a beam of current of 20 µA. The overall volume of the target solution comprising zinc or $^{68}$Zinc may be comprised between 0.5 mL and 10 mL.

After irradiation of the target (10), the irradiated target solution is received in a collection vial. There, the irradiated target is diluted (step a) in water to obtain a diluted solution (20). The dilution of the irradiated target solution is at least 5 volume times the volume of the solution comprising the irradiated target. In a preferred embodiment, the irradiated solution target (10) is diluted at least 10 times. For example, when the overall volume of the irradiated target solution comprising zinc is around 1 mL, the volume of the diluted solution (20) is around 5 mL. In a preferred embodiment the dilution of the irradiated target solution is comprised between 5 and 15 volume times, more preferably between 10 and 15 volume times. The inventors have surprisingly found that the process is less efficient when lower dilution volumes than 5 volume times are used. Moreover, higher volumes increase process time, and thus loss of Gallium-68 isotope by radioactive decay.

This step of dilution allows achieving high $^{68}$Gallium adsorption yields into a strong cation exchanger (30). Indeed, over 90% of the total $^{68}$Gallium comprised in the diluted solution (20) is adsorbed on the strong cation exchanger (30) during the step of feeding (step b) the diluted solution into the strong cation exchanger (30). When one dilutes the irradiated solution with a lower volume times, adsorption of $^{68}$Gallium into the strong cation exchanger is reduced, and the overall yield of the process is therefore lower.

Once the irradiated target is diluted in water, the diluted solution (20) is afterwards fed (step b) into a strong cation exchanger (30) where the $^{68}$Gallium isotope is adsorbed (or trapped) on the strong cation exchanger (also known as SCX) (30). By fed, it must be understood that, for example, the diluted solution (20) is passed through the exchanger (30). The exchanger (30) may be a strong cationic column loaded with a strong acid cation resin containing DVB (divinylbenzene). For example commercial resin DOWEX® 50WX8 (Dow Chemical Co., Midlands, Mich., USA) or AG 50W-X8 (BioRad Laboratories, Hercules, Calif., USA) and the likes may be used. The strong cation exchanger (30) may be preconditioned firstly with 3M hydrochloric acid solution and then by washing the exchanger with water. For example, for about 1400 mg of resin exchanger, between 3 mL and 10 mL, preferentially about 5 mL, of hydrochloric acid 3M solution followed by between 5 mL and 15 mL, preferentially about 10 mL, of water may be used during the preconditioning of the exchanger (30), eventually followed by air in order to dry the exchanger. Of course, a greater volume of water may be used when preconditioning the exchanger.

After adsorption of $^{68}$Gallium isotope on the strong cation exchanger (30), the exchanger is washed (step c). In a preferred embodiment, the exchanger is washed with water (100), and more preferentially with chelexed water to avoid the presence of any undesirable contaminants. This washing step allows removing certain type of contaminants, like $^{11}$C and $^{13}$N isotopes. The volume of the washing solution may be dependent from the volume of the irradiated target (10) and/or the weight of the exchanger (30). For example, when the weight of the exchanger (30) is about 1400 mg, about 5 mL of water may be used to wash the strong cation exchanger (30). Of course, a greater volume may be used. It should also be understood that a plurality of washing steps may be performed.

After this washing step, Zinc isotopes are eluted (step d) from the strong cation exchanger. The Zinc isotopes may be recovered in a vial for optional Zn purification and reuse. The Zinc elution solution (200) used for this step should comprise acetone. In a more preferred embodiment, the Zn elution solution (200) is 80% acetone, and in a more preferred embodiment, the Zn elution solution (200) is 0.5 M hydrobromic acid (HBr) in 80% acetone solution. The volume of the Zn elution solution (200) needed to perform this washing step may be dependent from the volume of the irradiated target (10) and/or the weight of the strong cation exchanger (30) and/or the molarity of the acetone solution (300). For example, when the weight of the exchanger is about 1400 mg and the solution is 80% acetone, between 10 mL and 50 mL, preferentially about 30 mL, of the Zn elution solution (200) may be used. Of course, greater volume of the Zn elution solution may be used.

After the step of elution of Zinc, a further step of washing (step e) the strong cation exchanger is performed. This step may be performed with water or chelexed water, like the first washing step described above. The purpose of this step is to remove traces of acetone and eventually HBr when the Zn elution solution (200) is hydrobromic acid in 80% acetone solution.

After the step d) of elution of the Zinc from the strong cation exchanger (30) and the step of washing the SCX, a step of elution (step f) of the $^{68}$Gallium from the strong cation exchanger (30) is performed to obtain an eluted solution (40). A hydrochloric acid solution (300) should be used when performing this step of the process. In a preferred embodiment, the hydrochloric acid solution (300) has a molarity comprised between 1 M and 5 M, preferentially between 2 M and 4 M, and more preferentially between 2.8 M and 3.2 M, and still more preferentially a molarity about 3 M. The volume of the hydrochloric acid solution (300) may be dependent from the weight of the strong cation exchanger (30) and/or the molarity of the hydrochloric acid solution (300). For example, when the weight of the strong cation exchanger (30) is about 1400 mg and the molarity of the hydrochloric acid solution (300) is about 3 M, between 5 mL and 10 mL, preferentially about 7 mL, of hydrochloric acid solution may be used when performing this step of the process. Of course, greater volume of hydrochloric solution may be used when one performs this step of the process. The eluted solution (40) is collected into a collection vial or reservoir.

In a preferred embodiment of the process, an optional additional step of complementing the eluted solution (40) with another hydrochloric acid solution (350) is performed before feeding the eluted solution (40) into the strong anion exchanger (also known as SAX) (50). This hydrochloric acid solution (350) may be about 12 M. The purpose of the complementation is to decrease/adjust the pH of the eluted solution (40). In a more preferred embodiment, hydrochloric acid is added to the eluted solution (40) until the molarity of the hydrochloric acid in the complemented solution is comprised between 7 M and 10 M, preferentially between 7.5 M and 9 M, more preferentially between 7.5 M and 8.5 M, and most preferentially about 8 M.

The eluted solution (40) or the complemented solution comprising $^{68}$Gallium is thereafter fed (step g) into a strong anionic exchanger (SAX) (50). For example, this exchanger (50) may be a strong anionic column loaded with a strong anion resin like BIORAD AG1X8 (Bio-Rad laboratories, Hercules, Calif., USA) and the like. The strong anion exchanger (SAX) (50) may be preconditioned with 8M HCl before feeding (step g) the eluted solution (40) or the complemented solution into the strong anion exchanger (SAX) (50). In a preferred embodiment, the strong anion exchanger (SAX) (50) is preconditioned with chelexed water followed by hydrochloric acid solution with a molarity comprised between 7 M and 10 M, preferentially between 7.5 M and 9 M, more preferentially between 7.5 M and 8.5 M, and most preferentially about 8 M.

Then, the strong anion exchanger (SAX) (50) is washed (step h) in order to elute impurities like traces of hydrochloric acid and/or to ensure correct pH of the final solution (60). The washing solution used in this step (step h) may be water. In a preferred embodiment, this step is performed with ethanol solution, like 95% ethanol (400). The volume of the washing solution may be dependent on the mass of the strong anion exchanger and/or the molarity of the ethanol solution. For example, when the mass of the strong anion exchanger is about 400 mg, between 0.5 mL and 2 mL, preferentially about 1 ml, of 95% ethanol solution may be used to perform the washing step (step h).

Following this washing step, the $^{68}$Gallium isotope is finally eluted (step i) from the strong anion exchanger (50). A solution of hydrochloric acid (400) is used to perform this step. In a preferred embodiment, the molarity of the hydrochloric acid solution (400) is comprised between 0.08 M and 1.2 M, more preferentially about 0.1 M. The final solution (60) comprises highly purified and concentrated $^{68}$Gallium isotope, preferentially in 0.1 M hydrochloric acid, and is ready to use for a further incorporation of $^{68}$Ga isotope into tracers molecules, like DOTA-TOC, DOTA-NOC, DOTA-TATE, PSMA-HBED-CC. The $^{68}$Ga isotope may be incorporated into tracer molecules that comprise a chelator selected among DOTA, PSMA, NOPO, TRAP, THP (tris-hydroxy-pyrydinones), PCTA, AAZTA, DATA, dedpa, FSC, NODAGA and the like.

The overall time to perform the process according to the invention is about 45 min. With the present process, highly pure and concentrated $^{68}$Ga isotope in 0.1 M hydrochloric acid solution is obtained. For example, when the weight of $^{68}$Zn in solution used is around 200 mg in Zinc-68 nitrate form, with a 30 min proton beam irradiation at a beam of current of 20 µA, the process according to the invention achieves more than 100 mCi of pure $^{68}$Ga. The final solution is ready to be used on labelling peptides.

The $^{68}$Ga isotope purified and concentrated according to the process of the invention may be incorporated into tracer molecules according to the following steps:

reacting the final solution (60) comprising $^{68}$Ga isotope with a required amount of a peptide dissolved in a suitable buffer at a pH comprised between 3.5 and 3.9 to obtain a radiolabelled-peptide, cooling the mixture comprising $^{68}$Ga and said peptide to a temperature below 40° C., purifying the radiolabelled-peptide on a C18 cartridge.

For example, the solution comprising highly purified and concentrated $^{68}$Gallium (in 0.1 M HCl) is fed into a pre-conditioned (1 mL of 4 M HCl, 10 mL of H2O) cation exchange SCX column. The column is dried with a stream of N2 to remove any traces of HCl. Thereafter, $^{68}$Ga is eluted. The elution solution should comprise acetone. In a more preferred embodiment, the elution solution is 98% acetone, and in a more preferred embodiment, the elution solution is 0.02M hydrochloric acid (HCl) in 98% acetone solution. The volume of the elution solution needed to perform this washing step may be dependent from the weight of the strong cation exchanger. For example, when the weight of column used is around 100 mg, about 1 mL of a mixture of acetone (98%)/HCl 0.02 M is fed directly into the reaction vial pre-loaded with the required amount of peptide dissolved in 1 mL of suitable buffer at pH comprised between 3.5 and 3.9. The total reaction volume is about 2 mL. The reaction mixture is then heated at 95° C. for 10minutes. After the reaction, the mixture is cooled by dilution with 5 mL of sterile water and with a steam of compressed air outside of reactor, before being loaded into the C18 SPE cartridge to a quantitative adsorption of the peptide on the column. A C18 column (or C18 cartridge) is a HPLC (high performance liquid chromatography) columns that use a C18 substance as the stationary phase. The inventors found that cooling the $^{68}$Ga-peptide mixture is critical as it reduces substantially the radiolabelled peptide losses during purification. After a washing step with 5 mL of sterile water the $^{68}$Ga-peptide complex is eluted from the cartridge with 1 mL of 75% ethanol followed by 9 mL of saline solution to obtain the very pure $^{68}$Ga-peptide. The product is then sterilized by filtration through a 0.22 µm membrane filter and transferred to the final vial. The final product is ready to use in a PET method.

Alternatively, the $^{68}$Ga isotope purified and concentrated according to the process of the invention may be incorporated into tracers molecules according to the following steps:

feeding the final solution (60) into a strong cation exchanger, drying the strong cation exchanger, eluting $^{68}$Gallium isotope from the strong cation exchanger with a mixture of acetone and hydrochloric acid to obtain a reaction solution comprising $^{68}$Gallium isotope, reacting the reaction solution comprising $^{68}$Ga isotope with a required amount of a peptide dissolved in a suitable buffer at a pH comprised between 3.5 and 3.9 to obtain a radiolabelled-peptide, cooling the mixture comprising $^{68}$Ga and said peptide to a temperature below 40° C., purifying the radiolabelled-peptide on a C18 cartridge.

The strong cation exchanger may be a strong cationic column loaded with a strong acid cation resin containing DVB (divinylbenzene). For example commercial resin DOWEX® 50WX8 (Dow Chemical Co., Midlands, Mich., USA) or AG 50W-X8 (BioRad Laboratories, Hercules, Calif., USA) and the likes may be used. The mixture of acetone and hydrochloric acid may be a acetone (98%)/Hydrochloric acid 0.02 N solution. About 1 mL of the mixture may be used to elute $^{68}$Gallium isotope.

The invention also concerns a disposable cassette able to perform the dilution, purification and concentration steps according to the method of the invention. A disposable cassette according to a first embodiment of the invention is illustrated on FIG. 2.

Figure 2:
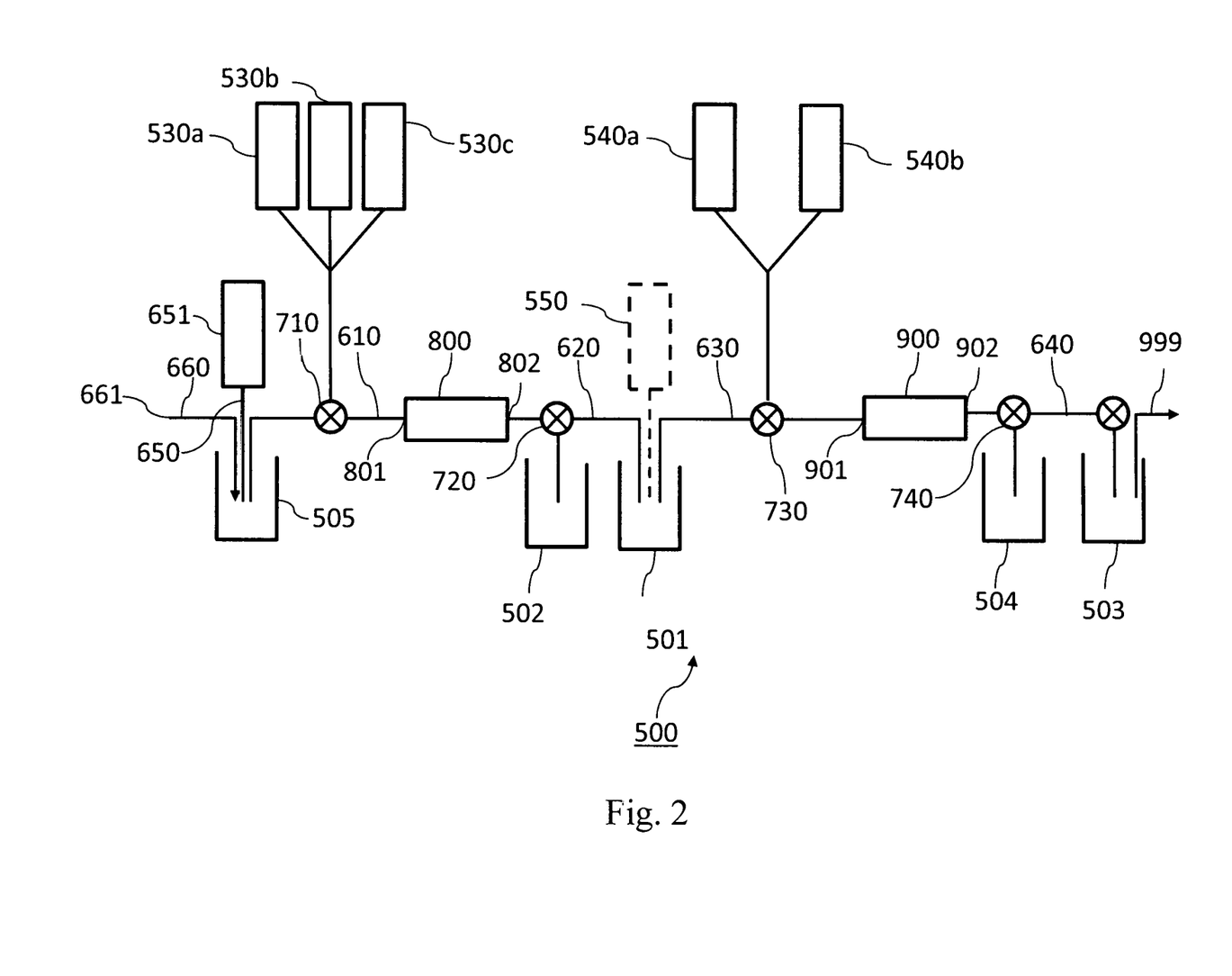
FIG. 2 shows a schematic view of a disposable cassette according to a first embodiment of the invention.

This disposable cassette comprises a dilution vial (505) connected by a fifth conduit (650) to a bottle (651) containing water. The disposable cassette (500) is furthermore characterized in that the dilution vial (505) is connected by a sixth conduit (660) to the outlet (661) of the $^{68}$Zn target. The disposable cassette (500) is furthermore characterized in that the first conduit (610) comprises a second end connected to the dilution vial (505).

By disposable cassette, it should be understood that the cassette may be plugged in and out of a device for synthesis of radiopharmaceuticals products from chemical reagents. The device for synthesis of radiopharmaceuticals may be a device that is able to perform the above described incorporation of $^{68}$Ga isotope into tracer molecules. The disposable cassette is dedicated to operate with different type of synthesizers driven by an automated controller. For example, the synthesizer may be the SYNTHERA® platform sold by ION BEAM APPLICATION, Louvain-La-Neuve, Belgium. The device may also be the one described in the patent EP1343533. This device enables the different chemical compounds for carrying out the synthesis of radiopharmaceutical compounds to be brought into contact during reaction and allows purification of the product. The device for synthesis of radiopharmaceutical compounds and the disposable cassette (500) when plugged to the device may be linked to an automaton which controls the various operations enabling the performance of the purification and concentration of $^{68}$Ga, and the synthesis of pharmaceutical compounds. Pump means may be located on the disposable cassette (500) and/or on the synthesizer. For example, the pump means may be syringe pumps connected to at least some of the conduits to draw and pump fluid through the conduits. A man skilled in the art is able to determine where such syringe pumps may be implanted on the disposable cassette. For example, a syringe pump may be implanted on each conduit. An automated controller is programmed to operate pumps and valves, and control the provisions of the various chemical reagents for a correct purification and concentration of the Gallium-68. For example, the liquid is pumped through the conduits by a vacuum or by a syringe pump. When a defined volume of the chemical reagent has reached to desired location (for example one of the cationic exchanger), a 3-way valve is actioned and the liquid is therefore pumped to a disposable vial (or waste vial) when the liquid is a washing liquid, or a liquid comprising impurities. When the liquid comprises the Gallium-68, the 3-way valve is activated allowing pumping the liquid to the elution vial or to the final solution vial. The disposable cassette (500) may comprise securing means which enable it to be fixed to the synthesizer. The securing means can take the form of fasteners arranged according to a precise configuration. It should be understood that, when the disposable cassette is connected to the synthesizer, both devices are in fluid communication through an outlet (999) of the cassette. The cassette is removable from the synthesizer. For example, the disposable cassette is cooperatively engaged with the synthesizer to drive the fluids from the output line of a cyclotron to the synthesizer. The steps of purification and concentration of the Gallium-68 are performed within the disposable cassette, while the incorporation of the Gallium-68 into radiopharmaceuticals is performed within the synthesizer. The disposable cassette (500) is removed after the synthesis run and may be replaced by a fresh cassette. Alternatively, some elements of the disposable cassette may be replaced, like the chemical reagents or the cation exchangers, while the other elements of the cassette are washed to remove any trace of the previous run. The disposable cassette (500) may comprise a rigid portion (e.g. an ABS plate) on which the various components of the disposable cassette (500) are arranged and fixed.

By chemical reagents, it should be understood the reagents used for purifying and concentrating $^{68}$Ga isotope, like water, acetone, Hydrochloric acid. In a more preferred embodiment, one first bottle (530a) comprises water; one other first bottle (530b) comprises acetone; and one other first bottle (530c) comprises hydrochloric acid. In a complementary embodiment, one second bottle (540a) comprises water and one other second bottle (540b) comprises hydrochloric acid.

The disposable device (500) may comprise a support plate, for example in ABS, for supporting the elements constituting the disposable device. The conduits (610, 620, 630, 640, 650, 660) may be flexible tubes like silicone tubes, channels molded or drilled in a support plate. The bottles may be pre-metered bottles. The conduits may be linked to mechanical means acting on the said conduits and enabling to monitor and control mechanically the transfer of the chemical reagents, the various solutions (irradiated solution target, diluted solution, eluted solution, final solution) between their respective compartments. For example, such mechanical means may comprise:

- pistons for forwarding a fluid from one vessel, vial or bottle to another,
- valves such as three-way valves for directing a fluid from one conduit to another conduit,
- compressed air or gas or law pressure of air or gas for forwarding a fluid from one vessel, vial or conduit to another,
- pumps,
- under the control of an automaton or a computer.

Once the final concentration step has taken place, the pure product is taken out from the disposable cassette and dispatched to a synthesizer that will incorporate Gallium-68 into radiopharmaceuticals.

In a more preferred embodiment, the disposable cassette (500) furthermore comprises another optional bottle (550) containing hydrochloric acid connected directly to the elution vial (501). This allows for complementation of the eluted solution with hydrochloric acid before feeding the eluted solution into the strong anion exchanger (900).

Figure 3:
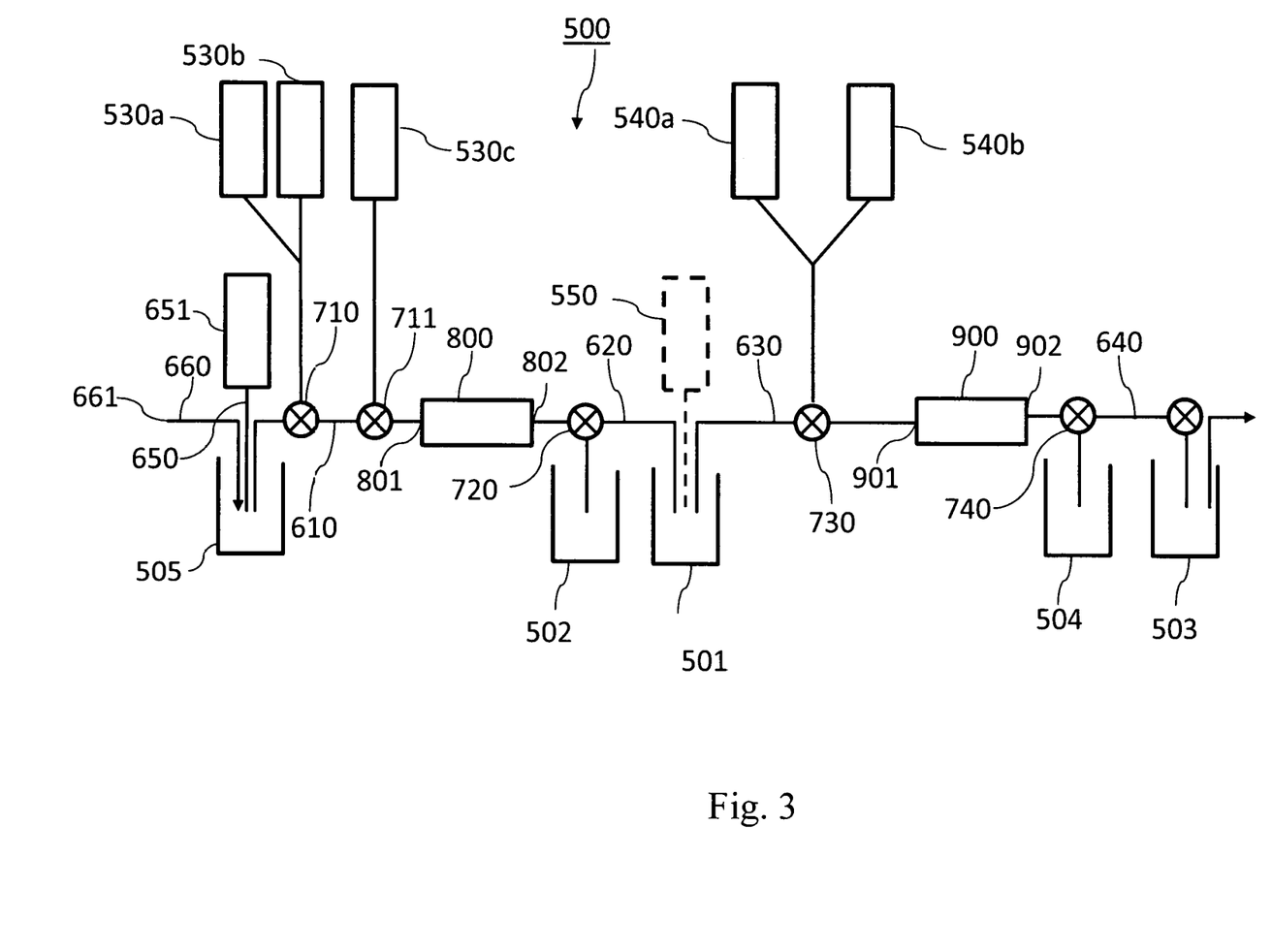
FIG. 3 shows a schematic view of a disposable cassette according to a second embodiment of the invention.

In a more preferred embodiment, illustrated on FIG. 3, the first conduit comprises two first 3-way valves (710, 711). One of the first 3-way valves (710) is connected to at least two bottles of reagent (530a, 530b). The other first 3-way valve (711) is connected to a third bottle of reagent (530c). This embodiment allows the separation of reagents reserved for washing the strong cation exchanger (800) and removing impurities, like $^{68}$Zn, from the strong cation exchanger (800) on one hand, and the reagents, like hydrochloric acid, reserved for eluting $^{68}$Ga isotope from the strong cation exchanger (800). The eluted solution contains less impurity when the disposable cassette (500) according to this embodiment is used.

The terms and descriptions used herein are set forth by way of illustration only and are not meant as limitations. Those skilled in the art will recognize that many variations are possible within the spirit and scope of the invention as defined in the following claims, and their equivalents, in which all terms are to be understood in their broadest possible sense unless otherwise indicated. As a consequence, all modifications and alterations will occur to others upon reading and understanding the previous description of the invention. In particular, dimensions, materials, and other parameters, given in the above description may vary depending on the needs of the application.

The present invention has been described in terms of specific embodiments, which are illustrative of the invention and not to be construed as limiting. More generally, it will be appreciated by persons skilled in the art that the present invention is not limited by what has been particularly shown and/or described hereinabove.

Reference numerals in the claims do not limit their protective scope.

Use of the verbs "to comprise", "to include", "to be composed of", or any other variant, as well as their respective conjugations, does not exclude the presence of elements other than those stated.

Use of the article "a", "an" or "the" preceding an element does not exclude the presence of a plurality of such elements.

What is claimed is:

1. A process for producing and purifying $^{68}$Gallium radioisotope, the process comprising:
    irradiating a target containing a target solution comprising zinc using an accelerated particle beam;
    diluting the irradiated target solution with water;
    feeding the diluted target solution into a strong cation exchanger;
    washing the strong cation exchanger;
    eluting zinc isotopes from the strong cation exchanger with a zinc elution solution including acetone;
    washing the strong cation exchanger;
    eluting $^{68}$Gallium isotope from the strong cation exchanger with hydrochloric acid solution to obtain an eluted solution;
    feeding the eluted solution into a strong anion exchanger,
    washing the strong anion exchanger; and
    eluting $^{68}$Gallium isotope from the strong anion exchanger with hydrochloric acid solution to obtain a final solution
    wherein the irradiated target solution is diluted between 5 and 15 volume times with water.

2. The process according to claim 1, wherein the irradiated target solution is diluted from 10 to 15 volume times with water.

3. The process according to claim 1, further comprising:
complementing the eluted solution with another hydrochloric acid solution to obtain a complemented solution, wherein the complementing is performed before feeding the eluted solution into the strong anion exchanger.

4. The process according to claim 3, wherein the complemented solution includes a molarity in hydrochloric acid between 7 M and 10 M.

5. The process according to claim 1, wherein the accelerated particle beam is a proton beam produced by a cyclotron.

6. The process according to claim 1, wherein the strong cation exchanger is preconditioned with water before feeding the diluted target solution into the strong cation exchanger.

7. The process according to claim 1, wherein eluting zinc isotopes from the strong cation exchanger is performed with a solution of acetone 80%/HBr 0.5 M.

8. The process according to claim 1, wherein the final solution includes $^{68}$Gallium in a hydrochloric acid solution of molarity between 0.08 M and 1.2 M.

9. The process according to claim 1, wherein the strong anion exchanger is preconditioned with hydrochloric acid solution before feeding the eluted solution into the strong anion exchanger.

10. The process according to claim 1, wherein the target solution comprising zinc further includes a zinc salt diluted in nitric acid or hydrochloric acid, wherein the zinc salt is selected from the group consisting of zinc nitrate, zinc chloride, zinc chlorate, zinc bromide, zinc iodide or zinc sulfate.

11. The process according to claim 1 further comprising:
reacting the final solution including $^{68}$Gallium isotope with a peptide dissolved in a buffer at a pH between 3.5 and 3.9 to obtain a radiolabelled-peptide;
cooling the radiolabelled-peptide to a temperature below 40° C.; and
purifying the radiolabelled-peptide on a C18 column.

12. The process according to claim 2, further comprising:
complementing the eluted solution with another hydrochloric acid solution to obtain a complemented solution, wherein the complementing is performed before feeding the eluted solution into the strong anion exchanger.

13. The process according to claim 2, wherein the final solution includes $^{68}$Gallium in a hydrochloric acid solution of molarity between 0.08 M and 1.2 M.

14. The process according to claim 3, wherein the strong cation exchanger is preconditioned with water before feeding the diluted target solution into the strong cation exchanger.

15. The process according to claim 3 further comprising:
reacting the final solution including $^{68}$Gallium isotope with a peptide dissolved in a buffer at a pH between 3.5 and 3.9 to obtain a radiolabelled-peptide;
cooling the radiolabelled-peptide to a temperature below 40° C.; and
purifying the radiolabelled-peptide on a C18 column.

16. The process according to claim 4, wherein the strong cation exchanger is preconditioned with water before feeding the diluted target solution into the strong cation exchanger.

17. The process according to claim 4, wherein the accelerated particle beam is a proton beam produced by a cyclotron.

18. The process according to claim 6 further comprising:
reacting the final solution including $^{68}$Gallium isotope with a peptide dissolved in a buffer at a pH between 3.5 and 3.9 to obtain a radiolabelled-peptide;
cooling the radiolabelled-peptide to a temperature below 40° C.; and
purifying the radiolabelled-peptide on a C18 column.

19. The process according to claim 7, wherein the strong anion exchanger is preconditioned with hydrochloric acid solution before feeding the eluted solution into the strong anion exchanger.

20. The process according to claim 9, wherein the target solution comprising zinc further includes a zinc salt diluted in nitric acid or hydrochloric acid, wherein the zinc salt is selected from the group consisting of zinc nitrate, zinc chloride, zinc chlorate, zinc bromide, zinc iodide or zinc sulfate.

* * * * *